United States Patent [19]

Mitsui et al.

[11] 4,311,134

[45] Jan. 19, 1982

[54] FLUID FEEDING DEVICE FOR AN ENDOSCOPE

[75] Inventors: Kazuhiko Mitsui, Hachioji; Mototugu Ogawa, Chofu, both of Japan

[73] Assignee: Olympus Optical Co., Ltd., Tokyo, Japan

[21] Appl. No.: 39,366

[22] Filed: May 16, 1979

[30] Foreign Application Priority Data

May 19, 1978 [JP] Japan .............................. 53-67350[U]
May 19, 1978 [JP] Japan .............................. 53-67351[U]
May 19, 1978 [JP] Japan .............................. 53-67352[U]

[51] Int. Cl.³ .......................... A61B 1/06; A61B 1/12
[52] U.S. Cl. ...................................................... 128/6
[58] Field of Search ........................ 128/3–8, 128/276

[56] References Cited

U.S. PATENT DOCUMENTS

| | | | |
|---|---|---|---|
| 2,173,637 | 9/1939 | Riedener | 128/276 |
| 3,749,090 | 7/1973 | Stewart | 128/276 |
| 3,830,225 | 8/1974 | Shinnick | 128/4 |
| 3,903,877 | 9/1975 | Terada | 128/6 |
| 4,215,476 | 8/1980 | Armstrong | 128/276 |

FOREIGN PATENT DOCUMENTS

| | | | |
|---|---|---|---|
| 47-34000 | 10/1972 | Japan | 128/6 |
| 48-10706 | 3/1973 | Japan | 128/6 |
| 48-34638 | 10/1973 | Japan | 128/6 |
| 53-36632 | 9/1978 | Japan | 128/6 |
| 53-36633 | 9/1978 | Japan | 128/6 |

*Primary Examiner*—Robert W. Michell
*Assistant Examiner*—Arthur S. Rose

[57] ABSTRACT

A fluid feeding device for an endoscope comprises an air pump, a sealed liquid reservoir, a first communication path communicating at one end with the air pump and at the other end with the upper portion of the liquid reservoir, a fluid raising tube extending through the liquid reservoir, a second communication path connected at one end to a fluid passage extending through an endoscope and at the other end to the upper end of the liquid raising tube, a liquid reservoir change-over valve provided between the liquid raising tube and the second communication path for connecting the liquid raising tube to the second communication path when the valve is set in a first position and disconnecting the liquid raising tube from the second communication path when the valve is set in a second position, and a fluid path selecting changeover valve disposed between the second communication path and the fluid path.

5 Claims, 22 Drawing Figures

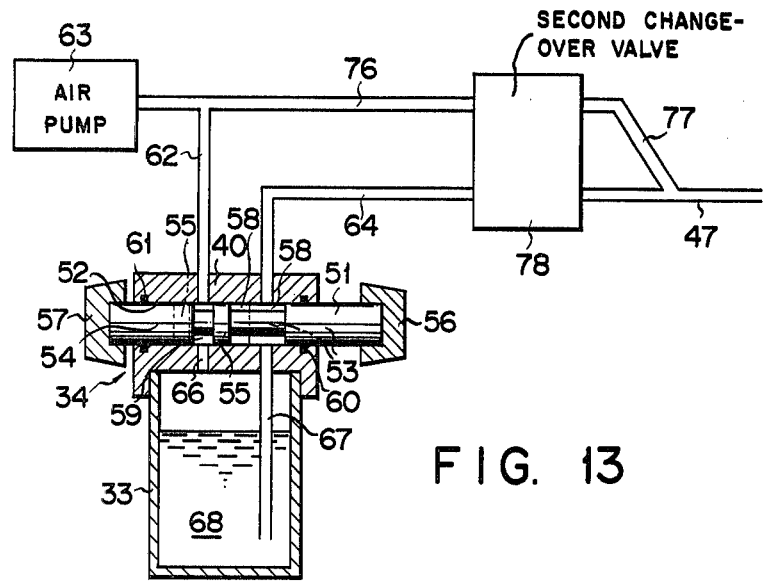
FIG. 13
FIG. 14
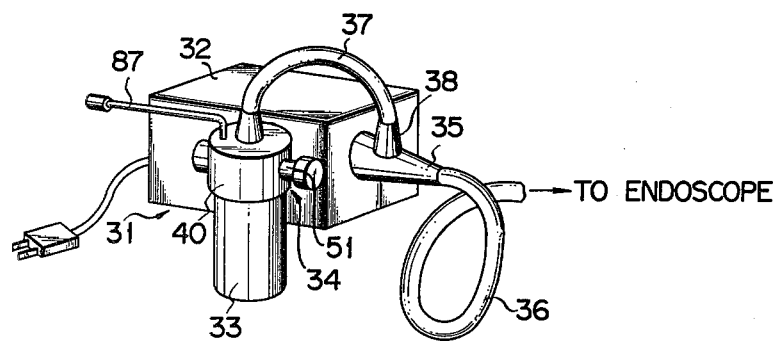
TO ENDOSCOPE 4,311,134

FLUID FEEDING DEVICE FOR AN ENDOSCOPE

BACKGROUND OF THE INVENTION

This invention relates to a fluid feeding device which feeds fluids selectively into a body cavity through an endoscope.

Generally an endoscope contains a water feeding tube. Through the water feeding tube, water is fed to the distal end of the endoscope to wash the body cavity, the observation window and illumination window of the endoscope, thereby preparing for the examination of the body cavity. Every time the endoscope is used, water must be removed or drained from the tube. Particularly in an endoscope with a film loaded in the distal end portion, water, if remaining in the water feeding tube, may flow into a camera when the distal end cap is removed, thus inevitably wetting the objective lens and other parts of the camera. In the endoscope of this type it is therefore absolutely necessary to drain or remove water from the water feeding tube before the distal end cap is taken off.

To drain water from a water feeding tube, the following steps are required in a prior art fluid feeding device. First, a connection tube between the water feeding tube and a water reservoir is disconnected from the water feeding tube. Then, its free end is covered with the cushion of a finger. And at the same time air is pumped into the water feeding tube until the inner wall of the water feeding tube is dried. These steps are not only time-consuming but also possibly cause the water to flow from one or both ends of the water feeding tube. Thus, the water may wet the distal end portion and/or the proximal end portion of the endoscope.

The prior art fluid feeding device is defective in that, when two fluids besides air, such as washing water, defoaming agent, tissue-coloring agent and compressed carbon dioxide gas, are selectively fed into a body cavity, or when a pressurized washing water is to be fed from feeding means other than the water reservoir, new communication means should be used in place of the connection tube. Selective use of two communication means is complicated, and the operator may erroneously feed a wrong fluid into the body cavity. Further, use of two communication means hinders miniaturization of the fluid feeding device. The device is inevitably larger in size particularly when two liquids are used and two reservoirs are required.

SUMMARY OF THE INVENTION

It is an object of this invention to provide a fluid feeding device for an endoscope, which can easily drain water or other liquid from a liquid feeding tube.

Another object of this invention is to provide a fluid feeding device for an endoscope, which can selectively feed at least two different liquids into a body cavity.

Still another object of this invention is to provide a fluid feeding device for an endoscope, which has a small size.

According to this invention there is provided a fluid feeding device for an endoscope, which comprises an air pump; a sealed liquid reservoir; a first communication path communicating at one end with the air pump and at the other end with the upper portion of the liquid reservoir; a liquid raising tube disposed having one end disposed in the lower portion of the reservoir and the other end opened; a second communication path communicating at one end with said other end of the liquid raising tube and at the other end with an endoscope fluid passage extending through an endoscope; a liquid reservoir change-over valve connected between said other end of the liquid raising tube and said one end of the second communication path for connecting the liquid raising tube to the second communication path when the valve is set in a first position and disconnecting the liquid raising tube from the second communication path when the valve is set in a second position; and change-over valve means connected between the endoscope fluid passage and said other end of the second communication path for allowing the endoscope fluid passage to communicate with the second communication path.

BRIEF DESCRIPTION OF THE DRAWING

This invention can be fully understood from the following detailed description with reference to the accompanying drawings in which:

FIG. 13 is a vertical cross sectional view of another embodiment of this invention;

FIG. 14 is a perspective view of still another embodiment of this invention;

DESCRIPTION OF THE PREFERRED EMBODIMENTS

Figure 1:
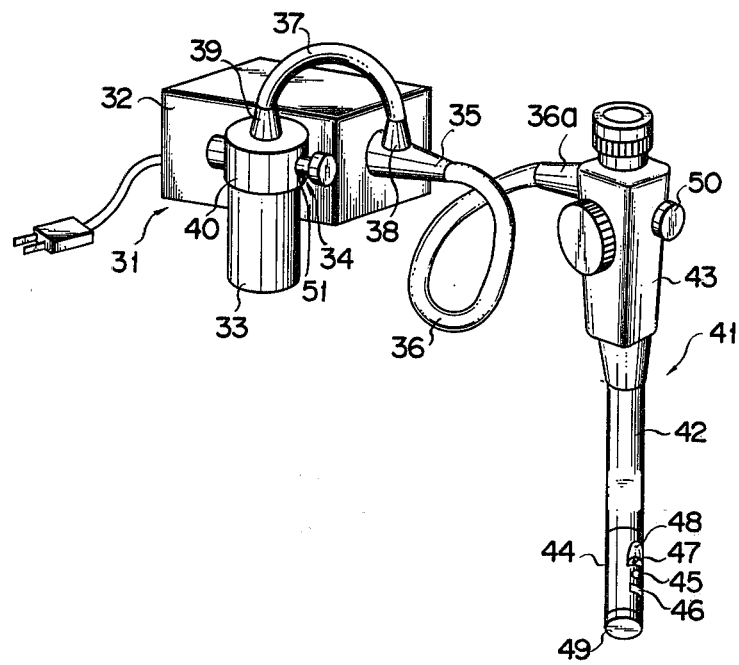
FIG. 1 is a perspective view of a fluid feeding device according to this invention.

In the accompanying drawings, like reference numerals designate like or similar parts.

Referring now to FIG. 1, a fluid feeding device 31 comprises a box-like housing 32 with an air pump provided in it, a liquid reservoir 33 detachably secured to a side wall of the housing 32 and containing a washing water, and a liquid reservoir change-over switching valve 34 covering the top of the reservoir 33 in a fluid tightness. Detachably or fixedly secured to another side of the housing 32 is a connector 35 by which one end of a protective outer tube 36 is connected to the housing 32. Another protective outer tube 37 is detachably or fixedly connected at one end to the connector 35 by means of a connector 38 and at the other end to the top of the housing 40 of the valve 34 by means of a connector 39. It will later be described how the protective outer tubes 36 and 37 function.

Figure 2:
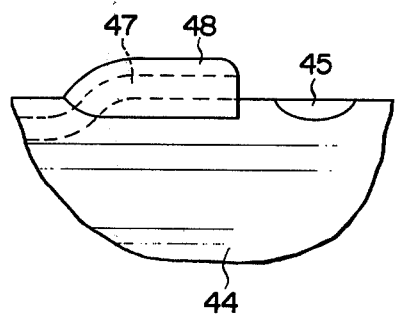
FIG. 2 is a side elevational view of the fluid outlet portion of the fluid passage in an endoscope shown in FIG. 1.

An endoscope 41 used with the fluid feeding device 31 comprises a sheath 42, an operation section 43 secured to one end of the sheath 42 and a rigid distal end portion 44 fixed to the other end of the sheath 42. The distal end portion 44 is provided with an objective lens 45, an illumination window 46 and a swelled portion 48. As shown in FIG. 2, the swelled portion 48 contains an end portion of an endoscope fluid passage 47 which extends through the sheath 42 from the operation section 43. The passage 47 opens at the end wall of the portion 48 so as to flow the fluid in the passage 47 on the objective lens 45 and the illumination window 46. A cap 49 is detachably connected to the forward end of the rigid distal end portion 44. After the cap 49 is removed from the distal end portion 44, a film cassette can be set or replaced in a photographing chamber (not shown) provided within the rigid distal end portion 44 as a prior art endoscope. On one lateral wall of the operation section 43, there is provided a push button 50 for actuating a liquid path switching valve, which will later be described. The other end of the protective outer tube 36 is detachably connected to another side wall of the operation section 43 by means of a connector 36a. The endoscope 41 has an identical construction with the known type except that it is provided with the fluid passage 47. Thus, its construction is not further described here.

Figure 3:
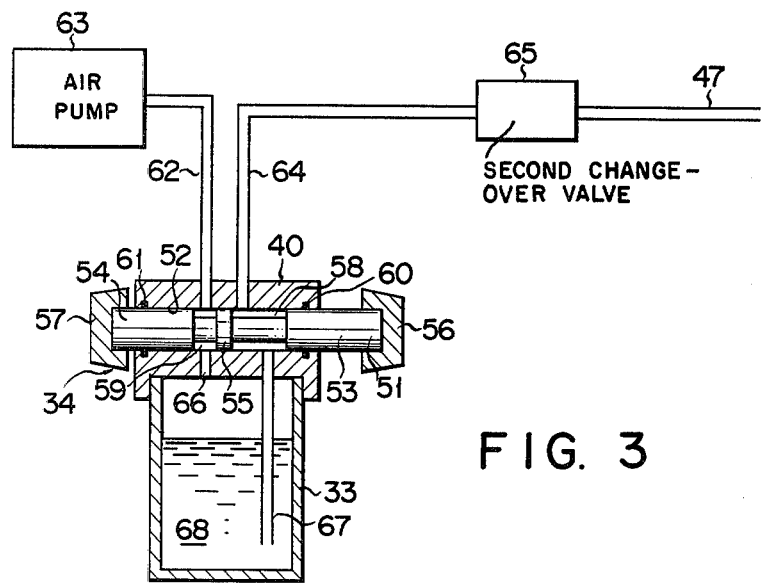
FIGS. 3 and 4 are vertical cross sectional views of the device shown in FIG. 1, showing the construction and function of the device.
Figure 4:
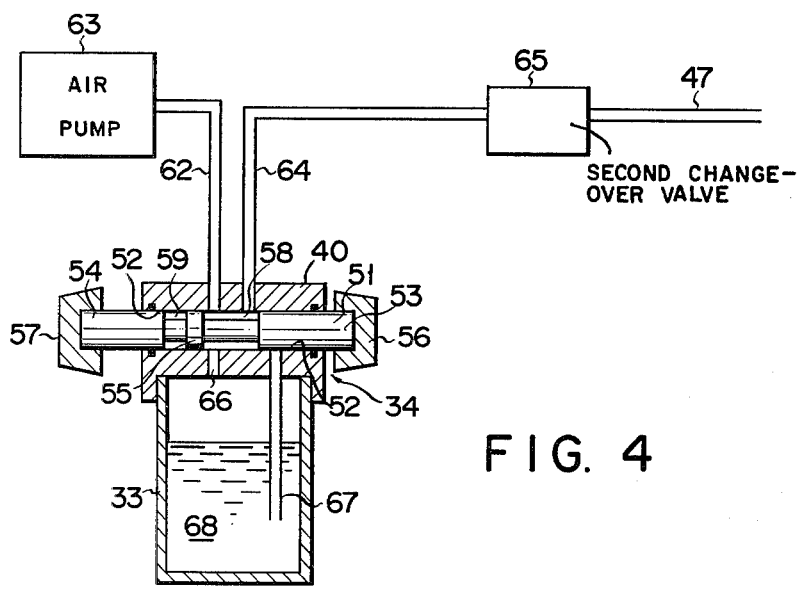

As shown in FIGS. 3 and 4, the liquid reservoir switching valve 34 is a kind of spool valve and comprises the cylindrical housing 40 which also serves as a lid covering the liquid reservoir 33 in a fluid-tight fashion and a spool 51 which is reciprocatingly slidable in a bore 52 diametrically penetrating the housing 40. The spool 51 comprises two longer end lands 53 and 54 and a shorter intermediate land 55. Two push buttons 56 and 57 are respectively attached to the corresponding outer ends of the lands 53 and 54. Further, the spool 51 has an annular groove 58 between the lands 53 and 55 and another annular groove 59 between the lands 54 and 55. In the valve housing 40, a pair of O-rings 60 and 61 surround the end lands 53 and 54, respectively, so that they provide a fluid-tight enagagement between the housing 40 and the spool 51.

A communication tube or path 62 communicates at one end with an air pump 63 provided in the housing 32 (FIG. 1) and at the other end with the bore 52 of the valve housing 40. Another communication tube or path 64 communicates at one end with the bore 52 on the right side of the tube 62 and is connected at the other end to the fluid passage 47 of the endoscope 41 through a fluid path selecting changeover valve 65. Further, a fluid path 66 is formed in the valve housing 40 at a position diametrically opposite to the tube 62 with respect to the bore 52. A liquid raising tube 67 is disposed in the liquid reservoir 33 with one end opened to the bore 52 on the right side of the tube 64 and the other end disposed in the lower portion of the reservoir 33 so as to be immersed in washing water 68 in the reservoir 33.

When the spool 51 is set in an extremely right position (hereinafter called the "first position") as illustrated in FIG. 3, the communication tube 64 and the liquid raising tube 67 open to the annular groove 58, and the communication tube 62 and the fluid path 66 open to the annular groove 59. When the spool 51 is moved to an extremely left position (hereinafter called the "second position") as shown in FIG. 4, the upper end of the liquid raising tube 67 is closed by the end land 53, and both communication tubes 62 and 64 open to the annular groove 58 of the spool 51 and the liquid raising tube 67 is blocked by the end land 53.

The communication tubes 62 and 64 extend through the protective outer tubes 37 and 36, respectively, and are thus protected from damage.

Figure 5:
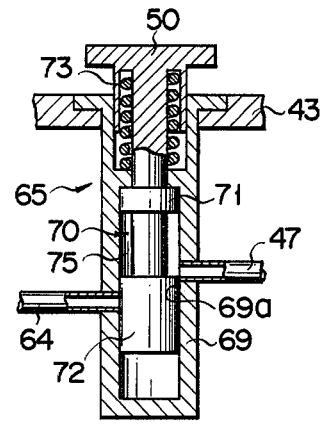
FIGS. 5 and 6 are vertical cross sectional views of a fluid path selecting changeover valve which is used in the embodiment of FIGS. 1, 3 and 4, the embodiment of FIGS. 7 and 8, the embodiment of FIGS. 15 and 16, the embodiment of FIG. 17, the embodiment of FIGS. 19 and 20 and embodiment of FIG. 21.
Figure 6:
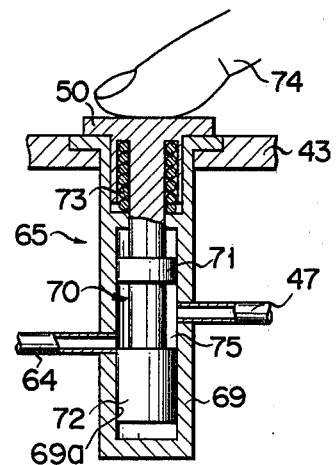

The change-over valve 65 connected to the liquid reservoir change-over valve 34 is constructed as illustrated in FIGS. 5 and 6. The valve 65 is a kind of spool valve and comprises a hollow cylindrical valve housing 69 and a spool 70 slidably inserted into a cylindrical bore 69a of the housing 69. The housing 69 is provided in the operation section 43 with one end fixed to said lateral wall of the operation section 43 of the endoscope 41. The spool 70 has a pair of lands 71 and 72 and the push button 50 is provided on one end disposed nearer said one end of the housing 70 and protrudes from said one lateral wall of the operation section 43. A coil spring 73 causes the button 50 normally to protrude from the operation section 43. An annular groove 75 is formed between lands 71 and 72. When the button 50 is not pushed or when the spool 70 is in a highest position (hereinafter called the "closed position") as illustrated in FIG. 5, the communication tube 64 is closed by the lower land 72. When the button 50 is pushed until the spool 70 reaches its lowest position (hereinafter called the "open position") as shown in FIG. 6, the communication tube 64 and the fluid passages 47 open to the annular groove 75, whereby they communicate with each other.

In operation, the spool 51 of the liquid reservoir change-over valve 34 is set in the first position, and then the air pump 63 is started. Then, compressed air flows from the pump 63 into the liquid reservoir 33 through the communication tube 62, the annular groove 59 and the fluid passage 66, thus applying a pressure on the washing water 68, When the valve 65 is set in the open position, the washing water 68 is introduced from the liquid reservoir 33 into the fluid passage 47 of the endoscope 41 through the liquid raising tube 67, the annular groove 58 and the communication tube 64, and then, the water 68 flows out of the swelled portion 48 so as to wash the objective lens 45, the illumination window 46 and the body cavity in which the endoscope 41 is inserted.

When the liquid reservoir change-over valve 34 is set in the second position and then the fluid path selecting change-over valve 65 is set in the open position, the compressed air flows through the communication tube 62, the annular groove 58, the communication tube 64 and the fluid passage 47 as shown in FIG. 4. In this case, the compressed air flows into the body cavity from the swelled portion 48 and dries the objective lens 45 and the illumination window 46 as well as the body cavity. The liquid reservoir change-over valve 34 is used to select one of two fluids. In this case, washing water 68 and compressed air are selected. And the valve 65 allows the selected fluid to be conducted into a body cavity whenever it is set in the open position.

Figure 7:
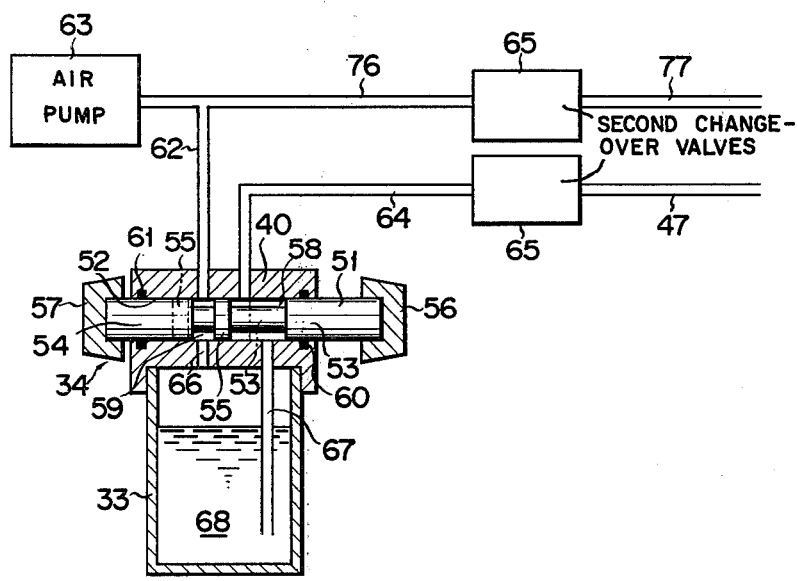
FIG. 7 is a vertical cross sectional view of another embodiment of this invention.

Referring now to FIG. 7, another embodiment of this invention will be described. A fluid feeding device of FIG. 7 differs from the device of FIGS. 3 and 4 only in that a communication tube or path 76 is branched from a communication tube 62 and connected to a fluid path 77 extending through an endoscope 41 (shown in FIG. 8) besides a fluid passage 47, via a fluid path selecting change-over valve 65 of the same structure as illustrated in FIGS. 5 and 6. The communication tube 76 and the fluid passage 77 are connected to the valve 65 in the same manner as the communication tube 65 and fluid passage 47 are connected to the valve 65 as illustrated in FIGS. 5 and 6.

As in the device of FIGS. 3 and 4, when a spool 51 of a liquid reservoir change-over valve 34 is set in the first position as indicated by solid lines, the communication tube 62 and a fluid path 66 open to an annular groove 59. At the same time, the communication tube 64 and a liquid raising tube 67 open to an annular groove 58. On the other hand, when the spool 51 is set in the second position as indicated by chain lines, the communication tubes 62 and 64 open to the annular groove 58, but the liquid raising tube 67 is closed by an end land 53 of the spool 51. When the valve 65 connected to the tube 64 is opened, air is conducted from the air pump 63 to the fluid passage 47 through the tube 62, the groove 58 and the tube 64, thereby draining water in the passage 47.

In operation, an air pump 63 is started, and the spool 51 is set in the first position. When the valve 65 connecting the communication tube 64 to the fluid passage 47 is set in the open position, washing water 68 flows from the reservoir 33 into the fluid passage 47 of the endoscope 41 under the air pressure applied to the water 68 in the liquid reservoir 33. By contrast, when the spool 51 is set in the second position and when the valve 65 connecting the communication tube 76 to the fluid passage 77 is set at the open position, the compressed air flows from the pump 63 into the fluid passage 77 of the endoscope 41 through the communication path 76, without flowing into the liquid reservoir change-over valve 34. The compressed air flows into a body cavity from a swelled portion 48 provided on the periphery of a rigid distal end portion 44 of the endoscope 41. At this time, the liquid raising tube 67 is closed by the end land 53 of the spool 51, and the washing water 68 is not fed into the body cavity even if the operator mistakenly opens the valve 65 connected to the communication tube 64.

Figure 9:
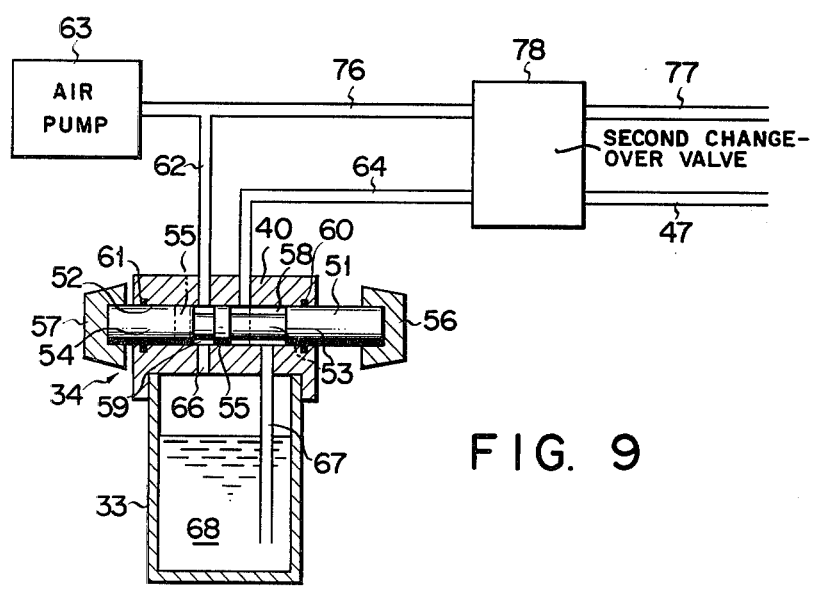
FIG. 9 is a vertical cross sectional view of another embodiment of this invention.
Figure 12:
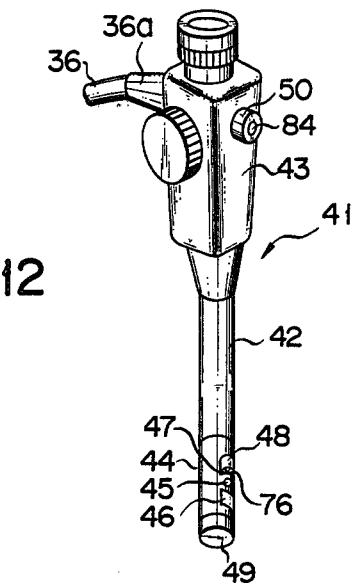
FIG. 12 is a perspective view of an endoscope provided with the fluid path selecting valve shown in FIGS. 10 and 11.
Figure 10:
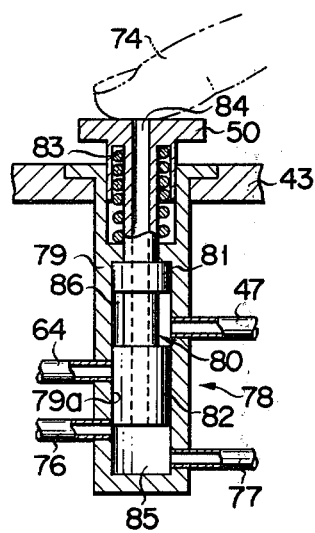
FIGS. 10 and 11 are vertical cross sectional views of a fluid path selecting valve which is used in embodiments of FIGS. 9, 12, 13, 18 and 22.
Figure 11:
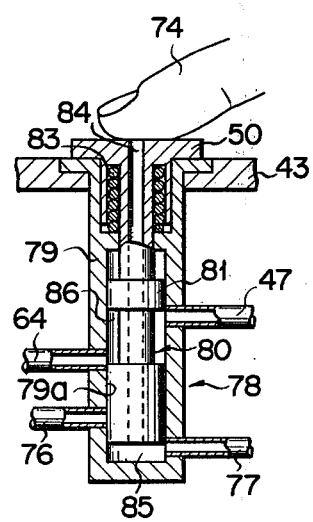

FIG. 9 shows another embodiment of this invention which differs in construction from the device of FIG. 7 only in that a fluid path change-over valve 78 is used in place of two valves 65. The valve 78 is a kind of spool valve, too. As shown in FIGS. 10 and 11, the valve 78 comprises a hollow cylindrical valve housing 79 having a cylindrical bore 79a and a spool 80 reciprocatingly inserted into the bore 79a. The housing 79 is provided in an operation section 43 of an endoscope shown in FIG. 12 with one end fixed to one lateral wall of the operation section 43. The spool 80 has a pair of lands 81 and 82 and push button 50 provided on one end nearer said one lateral wall of the operation section 43 so as to protrude therefrom. A coil spring 83 causes the button 50 normally to protrude from the operation section 43. An air passage 84 extends through the push button 50 and the spool 80. There remains a space between the bottom of the valve housing 79 and the lower end of the spool 80 when the spool 80 is in its lowest position as shown in FIG. 11. This space defines a communication chamber 85. Between the lands 81 and 82 of the spool 80 is formed an annular groove 86.

So long as the push button 50 is not dispressed by the cushion of a finger 74, as illustrated in FIG. 10, a communication tube 76 and a fluid passage 77 communicate with the chamber 85 and a communication tube 64 is closed by the lower land 82. When the button 50 is pushed as illustrated in FIG. 11, the communication tube 76 is closed by the lower land 82, while the communication tube 64 and a fluid passage 47 open to the annular groove 86.

When the button 50 is not depressed and the air passage 84 is not plugged, compressed air flows from an air pump 63 into the atmosphere through the communication tube 76, chamber 85 and air passage 84 and does not flow into a body cavity through the fluid passage 77 of the endoscope 41. When the air passage 84 is closed by, for example, the cushion of a finger 74 without depressing the push button 50, the compressed air flows into the body cavity through the communication path 76, the fluid passage 77 and a swelled portion 48 of the endoscope 41 without escaping into the atmosphere. When the button 50 is depressed while closing the air passage 84 as illustrated in FIG. 11, washing water 68 flows from a liquid reservoir 33 into the body cavity through the communication tube 64, the annular groove 86, the fluid passage 47 and the swelled portion 48. In this case, the communication tube 76 is closed by the lower land 82 of the spool 80, and the compressed air no longer flows into the body cavity.

FIG. 13 shows still another embodiment of this invention which differs from the device of FIG. 9 only in that a fluid passage 77 is connected to a fluid passage 47. The fluid passage 47 therefore functions to selectively supply compressed air and washing water to a body cavity.

Figure 15:
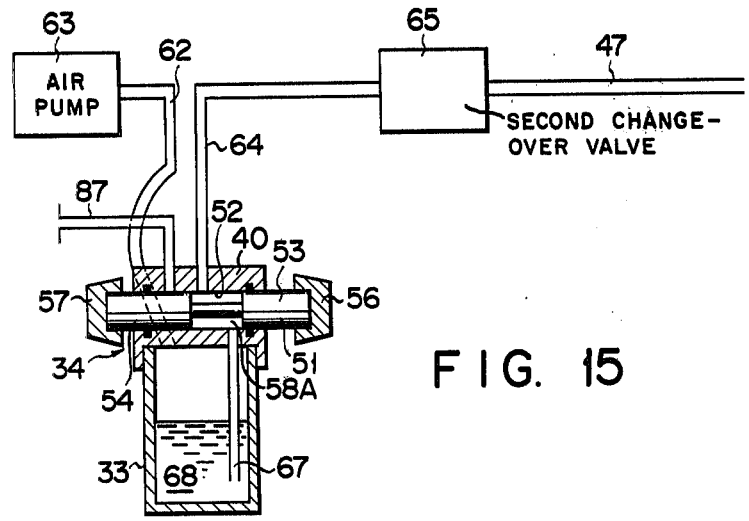
FIGS. 15 and 16 are vertical cross sectional views of the device shown in FIG. 14, showing the construction and function of the device.
Figure 16:
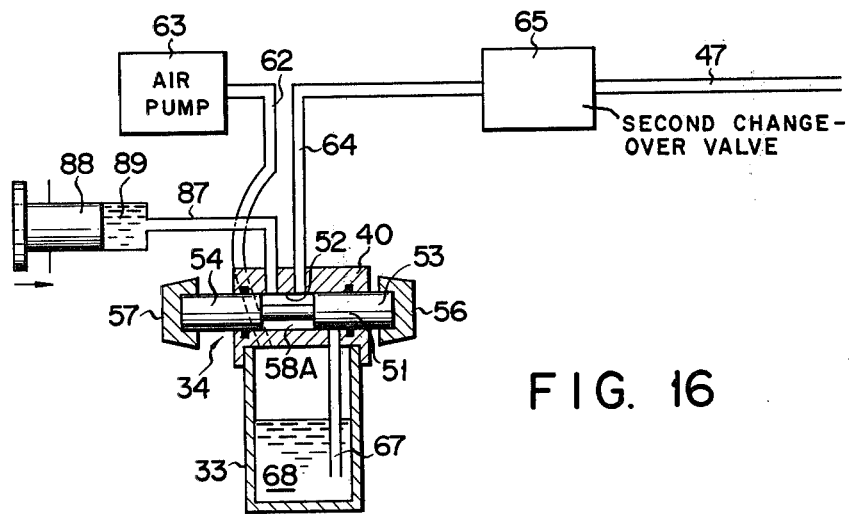

FIGS. 14, 15 and 16 show another embodiment of this invention, which can feed a fluid other than compressed air and washing water into a body cavity. This fluid feeding device differs from the device of FIGS. 1 to 4 in the following respects.

First, a communication tube 62 which communicates at one end with an air pump 63 has the other end penetrating the housing 32 of a liquid reservoir change-over valve 34 and connected directly to the upper portion of a liquid reservoir 33. Secondly, the spool 51 of the valve 34 has end lands 53 and 54 but does not have an intermediate land. Thirdly, a fluid feeding tube 87 communicates at one end with a cylindrical bore 52 of the housing 32 in which the spool 51 is reciprocatingly inserted.

When the spool 51 is set in the first position as shown in FIG. 15, a communication path 64 and a liquid raising tube 67 open to an annular groove 58A between the end lands 53 and 54. When a change-over valve 65 connecting the communication tube 64 to an endoscope fluid passage 47 is set in the open position under this condition, washing water 68 flows from the liquid reservoir 33 to the body cavity through a fluid passage 47. In this case, the fluid feeding tube 87 is closed by the end land 54. When the spool 51 is set in the second position as shown in FIG. 16, the communcation tube 64 and the fluid feeding tube 87 communicate with the annular groove 58A. So long as the spool 51 stays in the second position, washing liquid 89 may be fed by, for example, an injector 88 to a body cavity and an objective lens and illumination window of the endoscope 41 through the fluid feeding tube 87, annular groove 58A, tube 64 and fluid passage 47 when the valve 65 is set in the open position. Instead of the washing liquid 89, other fluids such as a defoaming agent, a structure coloring agent and carbon dioxide gas may be fed through the fluid feeding tube 87, annular groove 58A, tube 64 and fluid passage 47.

Figure 8:
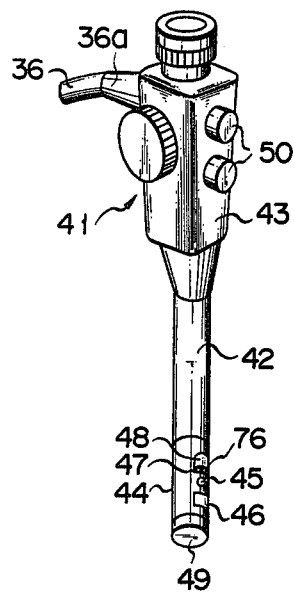
FIG. 8 is a perspective view of an endoscope for which the devices of FIGS. 7, 17 and 21 are used.
Figure 17:
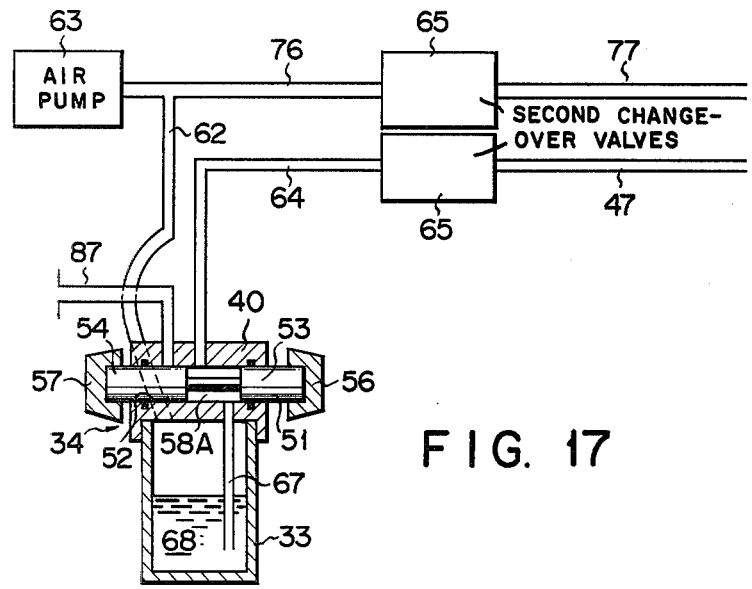
FIGS. 17 to 22 are vertical cross sectional views of further embodiments of this invention.
Figure 18:
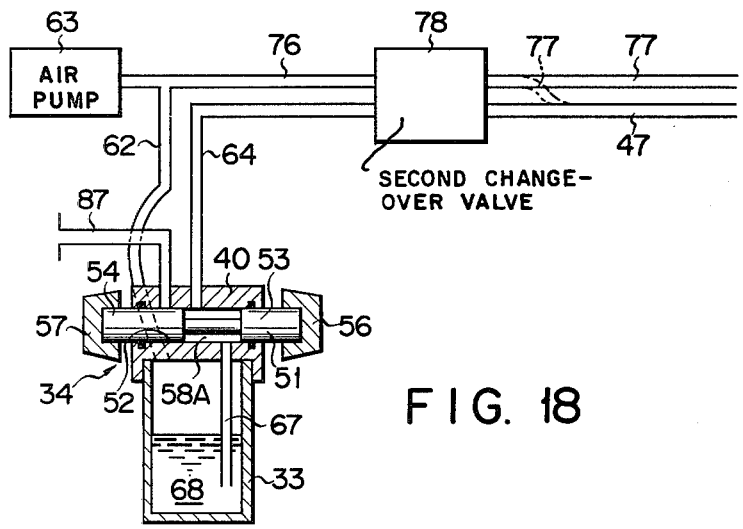

FIG. 17 shows still another embodiment of this invention which differs from the device of FIGS. 14 to 16 only in that a communication tube 76 is branched from a communication tube 62 and connected via a change-over valve 65 to a fluid passage 77 of such an endoscope 41 as shown in FIG. 8. FIG. 18 shows another embodiment of this invention which differs from the device of the FIG. 17 only in that a fluid path change-over valve 78 is used in place of two change-over valves 65. In both embodiments of FIGS. 17 and 18, the valves 65 and the valve 78 function exactly in the same way as in the device of FIG. 7 and the device of FIG. 9, respectively.

Figure 19:
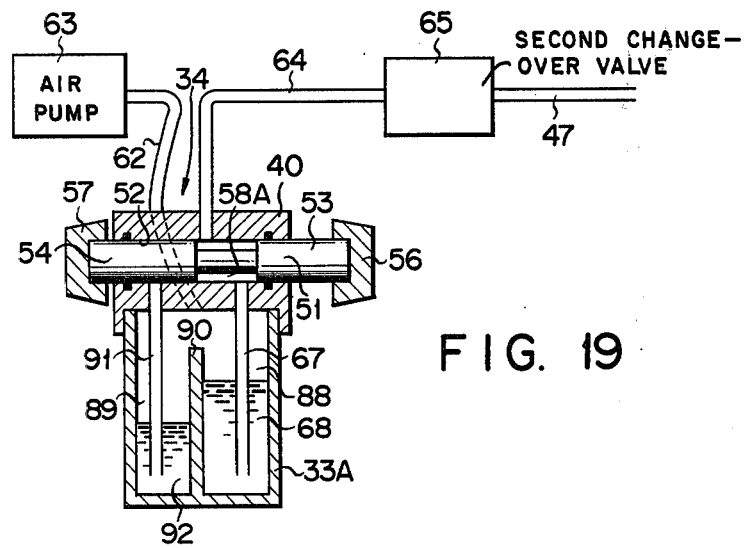
Figure 20:
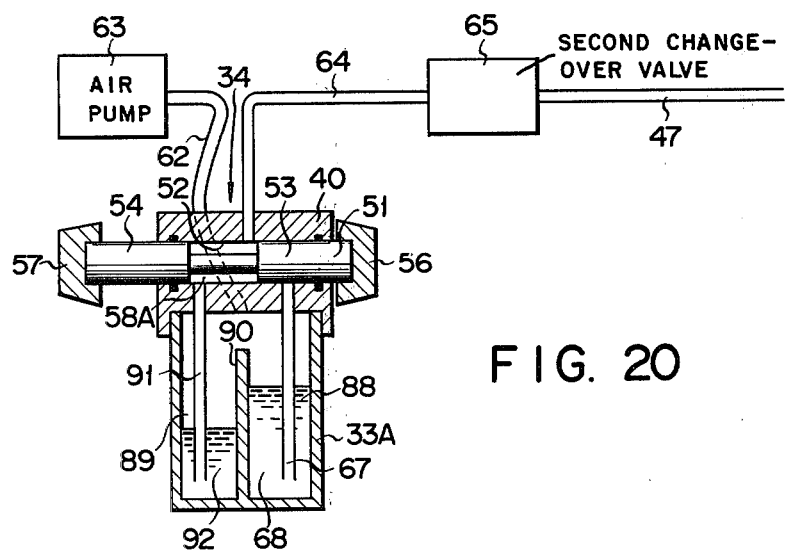

FIGS. 19 and 20 illustrate a further embodiment of this invention which, though largely similar to the device of FIGS. 15 and 16, differs in following respects. A liquid reservoir 33A is divided by a partition member 90 into two liquid chambers 88 and 89. The partition member 90 does not reach the lower surface of a valve housing 40 but is separated therefrom, thus providing a communication between the chambers 88 and 89. Two different liquid raising tubes 67 and 91 are provided in the chambers 88 and 89, respectively. The liquid raising tubes 67 and 91 communicate at the upper end with a bore 52 of the valve housing 32 and are immersed at the lower end in the liquids contained in the chambers 88 and 89. For example, a washing water is in the chamber 88, and a tissue-coloring agent is in the chamber 92.

When a spool 52 is set in the first position as shown in FIG. 19, the liquid raising tube 67 and a communication tube 64 communicate with an annular groove 58A between end lands 53 and 54. When a change-over valve 65 connecting a communication tube 64 to a fluid passage 47 in the endoscope 41 is in the open position in this condition, the washing water 68 flows from the chamber 88 through the communication tube 64 and the fluid passage 47. Since the liquid raising tube 91 in the chamber 89 is closed by the end land 54, the liquid 92 in the chamber 89 does not flow through the tube 64 and the fluid passage 47. By contrast, when the spool 51 is set in the second position as shown in FIG. 20, the liquid raising tube 67 in the chamber 88 is closed by the end land 53 whereas the liquid raising tube 91 in the chamber 89 and the communication tube 64 open to the annular groove 58A. When the valve 65 is in the open position, the agent 92 is supplied from the chamber 89 to the body cavity through the tube 64 and the fluid passage 47. Thus, two different liquids 68 and 92 are alternatively fed into a body cavity through the fluid passage 47 of such an endoscope 41 as illustrated in FIG. 1, by setting the liquid reservoir change-over valve 34 alternatively in the first and second positions. Since the liquid reservoir 33A is divided into two chambers, two different liquids are contained in the reservoir 33A without providing another liquid reservoir. The space occupied by the reservoir 33A is much smaller than the space occupied by two reservoirs.

Figure 21:
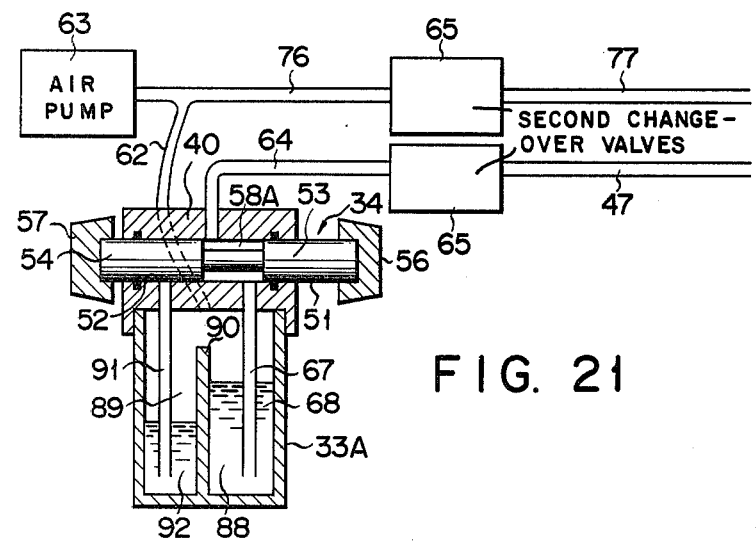

FIG. 21 shows another embodiment of this invention, which differs from the device of FIGS. 19 and 20 only in that a communication tube 76 is branched from a communication tube 62 and connected to a fluid passage 77 of an endoscope 41 shown in FIG. 8 through such a changeover valve 65 as illustrated in FIGS. 5 and 6. The fluid feeding device of FIG. 21 operates in the same manner as does the device of FIG. 17.

Figure 22:
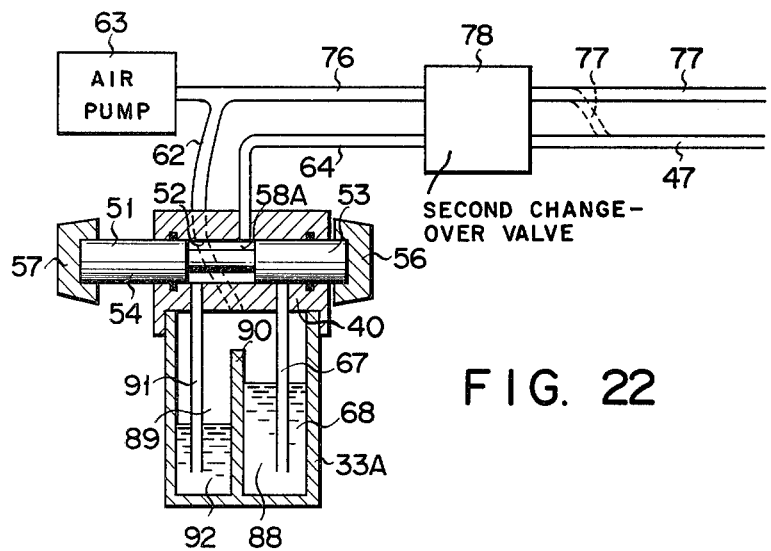

FIG. 22 shows still another embodiment of this invention, which differs in construction from the device of FIG. 21 only in that a fluid path change-over valve 78 of the same structure as illustrated in FIGS. 10 and 11 in place of two change-over valves 65. This embodiment operates in the same manner as the device of FIG. 18 does. A fluid passage 77 may be connected to a fluid path 47 as indicated by dotted lines.

What we claim is:

1. In combination, an endoscope having a fluid passage extending through said endoscope and a fluid feeding device disposed externally of said endoscope, said fluid feeding device comprising an air pump; a sealed liquid reservoir; a first communication path communicating at one end with the air pump and at the other end with an upper portion of the liquid reservoir; a liquid raising tube having one end disposed in a lower portion of the reservoir and the other end opened; a second communication path having two ends, one end being connected to the fluid passage; a first change-over valve for connecting the other end of the liquid raising tube to the other end of the second communication path when the first change-over valve is set in a first position and for disconnecting the liquid raising tube from the second communication path and causing the first communication path to communicate with the second communication path when the first change-over valve is set in a second position; said first change-over valve being a spool valve including a valve housing having a bore and a spool reciprocatingly inserted into the bore and comprising a first end land, a second end land, an intermediate land disposed between both the end lands, a first annular groove formed between the first end land and the intermediate land and a second annular groove formed between the second end land and the intermediate land, and there is provided a fluid path formed in the valve housing in alignment with the other end of the first communication path, said annular grooves being formed in such positions that, when the first change-over valve is in the first position, said other end of the liquid raising tube and said other end of the second communication path communicate with the first annular groove and the other end of the first communication path and said fluid path communicate with the second annular groove, and that, when the first change-over valve is in the second position, the other end of the liquid raising tube is closed by the first end land; and a second change-over valve disposed between the fluid passage and said one end of the second communication path for providing communication between the fluid passage and the second communication path when said second change-over valve is in an open position and for effecting disconnection between the second communication path and the fluid passage when said second change-over valve is set in a closed position.

2. The combination according to claim 1, wherein there is provided a third communication path having one end communicating with the air pump and the other end connected to a second fluid passage extending through said endoscope.

3. The combination according to claim 2, wherein there is a third change-over valve disposed between the second fluid passage and said other end of the third communication path for providing communication between the second fluid passage and the third communication path when said third change-over valve is in open position and for effecting disconnection between the third communication path and the second fluid passage when said third change-over valve is set in a closed position.

4. The combination according to claim 3, wherein said third change-over valve comprises a spool valve.

5. The combination according to claim 1, wherein said first change-over valve comprises a lid for sealingly covering the liquid reservoir.

* * * * *